_United States Patent_ [19]

Archibald et al.

[11] Patent Number: 5,420,311
[45] Date of Patent: May 30, 1995

[54] DIFLUOROAMINO OXETANES AND POLYMERS FORMED THEREFROM FOR USE IN ENERGETIC FORMULATIONS

[75] Inventors: Thomas G. Archibald, Fair Oaks; Gerald E. Manser, El Dorado Hills; John E. Immoos, Orangevale, all of Calif.

[73] Assignee: Aerojet General Corporation, Sacramento, Calif.

[21] Appl. No.: 82,332

[22] Filed: Jun. 24, 1993

Related U.S. Application Data

[62] Division of Ser. No. 939,350, Sep. 2, 1992, Pat. No. 5,272,249.

[51] Int. Cl.$^6$ ............................................. C07D 305/14
[52] U.S. Cl. ..................................... 549/510; 549/511
[58] Field of Search ............................. 549/510, 511

[56] References Cited

U.S. PATENT DOCUMENTS 4,330,475  5/1982  Adcock et al. .................... 549/380

Primary Examiner—C. Warren Ivy
Assistant Examiner—Ba K. Trinh
Attorney, Agent, or Firm—Townsend and Townsend Khourie and Crew

[57] ABSTRACT

This invention relates to novel oxetanes containing neopentyl difluoroamino groups. More specifically, mono- and bis-(difluoroaminomethyl)oxetanes are synthesized. These compounds are prepared by the direct fluorination of blocked neopentyl amines. These mono- and bis-(difluoroaminomethyl)oxetanes can be polymerized to form homopolymers and copolymers with load beating polyether backbones and highly energetic pendant groups. The homopolymers and copolymers of the present invention are useful as energetic binders in high-energy formulations, such as propellants, explosives, and gasifiers.

3 Claims, No Drawings

DIFLUOROAMINO OXETANES AND POLYMERS FORMED THEREFROM FOR USE IN ENERGETIC FORMULATIONS

STATEMENT OF GOVERNMENT INTEREST

This invention was made with Government support pursuant to Contract No. N0014-89-C-0281 awarded by the Department of the Navy. The Government has certain rights in this invention.

This is a Division of application Ser. No. 07/939,350, filed Sep. 2, 1992, now U.S. Pat. No. 5,272,249.

FIELD OF THE INVENTION

This invention relates to novel oxetanes containing neopentyl difluoroamino groups. More specifically, mono- and bis-(difluoroaminomethyl)oxetanes are synthesized. These compounds are prepared by the direct fluorination of blocked neopentyl amines. These mono- and bis-(difluoroaminomethyl)oxetanes can be polymerized to form homopolymers and copolymers with load bearing polyether backbones and highly energetic pendant groups. The homopolymers and copolymers of the present invention are useful as energetic binders in high-energy formulations, such as propellants, explosives, and gasifiers.

BACKGROUND OF THE INVENTION

High-energy solid formulations, such as propellants, explosives, and gasifiers, generally consist of particulate solids, such as fuel material, oxidizers, or both, held together by an elastomeric binder. These high-energy formulations also often include a plasticizer, such as a nitrate ester, which is a liquid prior to its incorporation into the formulation.

Organic compounds which contain nitrogen and fluorine are frequently used as fuel material and/or particulate oxidizers. These compounds are most suitable for making high-energy propellants because such compounds form gaseous HF as a decomposition product. During decomposition, the high heat of formation of HF is liberated to the surroundings, thereby doing mechanical work. Additionally, during the course of decomposition, fluorine is present as an oxidizing agent, and thus, no external source is required to complete oxidation.

Plasticizers are used in solid propellants and explosives to facilitate processing and increase flexibility and toughness, in addition to providing other benefits which vary with the nature and use of the formulation. Energetic or high-energetic plasticizers are those that provide energy in addition to flexibility and toughness, and their inclusion there/ore does not lessen the performance of the formulation. Considerations involved in the selection and use of plasticizers include compatibility with the other components of the formulation, including the primary energetic compounds and any binders present, the oxygen balance of the plasticizer, energy content, safety (i.e., stability with regard to detonation), and melting point. Plasticizers with melting points in a range which causes them to crystallize readily, for example, are of limited utility, since crystallization is detrimental to the plasticizer function and can adversely affect the mechanical properties of the propellant or explosive.

While the binder is an important means of maintaining the uniformity of the formulation and of holding it together, the binder material burns with substantially lower energy than the fuel. The binder thus imposes a limit on the energy content of the fuel material. One way of minimizing this limitation is to use a binder which release as much energy as possible when burning with the fuel. It is desirable, therefore, that the elastomeric binder have pendant groups which themselves are relatively high in energy.

Additionally, if a nitroester plasticizer is used in conjunction with the binder, nitroester-miscibility is required. Thus, in addition to being relatively high in energy, the polyethers and the elastomers formed therefrom should contain pendant groups which impart miscibility of the elastomer with the nitrate ester plasticizers. Nitro, nitrato, nitroamino and cyano groups are examples of pendant groups which impart nitrate ester-miscibility to the polymer and which have relatively high energies so as to contribute to the performance of the propellant.

Compounds containing two fluorine atoms bonded to nitrogen, i.e., a difluoroamino ($NF_2$) group, have been extensively studied as ingredients for propellants and explosives. The difluoroamino group has higher energy, higher positive heat of formation and greater thermal stability than the other frequently used pendant groups (e.g. the nitrato group). In addition to significantly improved energy content, the difluoroamino group strongly enhances the performance of formulations containing boron and aluminum as fuels.

Practical use of the difluoroamino group in propellants and explosives has been limited, however. In compounds known to date, the difluoroamino group was found to impart unacceptably high impact sensitivity or chemical instability to the compound. Due to the strong electron-withdrawing nature of the difluoroamino group, $NF_2$-containing compounds have been found to be unstable and readily lose HF to form nitriles when alpha hydrogens are present. Therefore, the use of $NF_2$-containing compounds in explosives and propellants has been limited to those compounds containing difluoroamino groups on a tertiary center prepared from tetrafluorohydrazine, or geminal di-difluoroamino groups prepared from strong acid solutions of difluoroamine. In both cases the resulting products are shock sensitive and expensive to prepare.

SUMMARY OF THE INVENTION

It has now been discovered that when a difluoroamino group is placed on a neopentyl carbon (i.e., a primary carbon directly bonded to a quaternary carbon), compounds are available that have remarkable stability and low impact sensitivity. When an aliphatic $NF_2$ group is located on a neopentyl carbon, there is sufficient steric hindrance to stabilize the $NF_2$ group and prevent liberation of HF. These neopentyl difluoroamino compounds may successfully be used in energetic formulations as elastomeric binders. It has also been discovered that compounds containing neopentyl difluoroamino groups are readily prepared in high yield by the direct fluorination of blocked neopentyl amines.

The present invention provides a variety of mono-$NF_2$-oxetanes and bis-$NF_2$-oxetanes. The mono-$NF_2$-oxetanes are optionally substituted with lower alkyls, nitro, nitrato, substituted nitroamines, and azido moieties. The invention further resides in energetic binders containing load bearing polyether backbones with high energy pendant groups, formed from the polymerization of the NF$_2$-substituted oxetanes.

Other advantages, objects, features and embodiments of the present invention will become apparent from the detailed description which follows.

DETAILED DESCRIPTION OF THE INVENTION AND PREFERRED EMBODIMENTS

Non-polymeric compounds in accordance with the present invention, include those having the general formula:

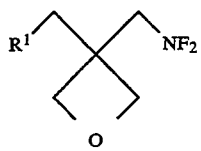 (I)

In Formula I, $R^1$ may be a functional group including, but not limited to, H, lower alkyls, NF$_2$, NO$_2$, ONO$_2$, N(R$^2$)NO$_2$ where $R^2$ is H or a lower alkyl, or N$_3$. Hereinafter where it is stated that $R^1$ is a difluoroamino group, it will be understood that other energetic groups, exemplified by nitro, nitrato, nitroamine or azido may also be used. The term "alkyl" is used herein to refer to substituents which are fully saturated hydrocarbon chains. The alkyl groups may be either straight-chain or branched-chain, limited only by steric hinderance. The term "lower alkyl" is used herein as it is used in the art, designating alkyl groups of a relatively small number of carbon atoms. Additionally, since alkyl groups do not add to the energetic character of the molecule, shorter alkyl groups (i.e., 1-4 carbons) are preferred.

Within the scope of Formula I, certain embodiments are preferred, namely those in which $R^1$ is H, CH$_3$, C$_2$H$_5$ or NF$_2$. Embodiments in which $R^1$ is either H or NF$_2$ are further preferred. Table I lists the properties of the mono- and bis-NF$_2$-substituted oxetanes. These NF$_2$-substituted oxetanes are useful for polymerization to form energetic binders.

The NF$_2$-substituted oxetanes, corresponding to Formula I, are particularly useful for polymerizing to form polyethers, which may be subsequently cured to form energetic binder materials. When polymerized, the resulting polyethers have the general formula:

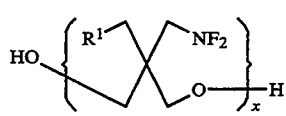 (II)

The polymer represented by Formula II may be a homopolymer or a copolymer with two or more different monomer units within the scope of Formula II, in any proportion, order or arrangement. For homopolymers, $R^1$ is the same group repeated along the length of the polymer chain, and is any of a variety of functional groups including, but not limited to, H, lower alkyl, NF$_2$, NO$_2$, ONO$_2$, N$_3$ or N(R$^2$)NO$_2$ where $R^2$ is H or a lower alkyl. For copolymers, $R^1$ differs along the polymer chain, with two or more different $R^1$'s selected from the above functional groups included in the structure. The symbol "x" represents an integer having a value selected so that the polymer has a molecular weight ranging from about 1,000 to 100,000.

Within the scope of Formula II, certain homopolymers are preferred, namely those in which $R^1$ is a functional group selected from the following: H, CH$_3$, C$_2$H$_5$ and NF$_2$; and x is an integer having a value such that the homopolymer has a molecular weight ranging from about 2,000 to 50,000. Further preferred are the homopolymers in which $R^1$ is either H or NF$_2$; and x is an integer having a value selected so that the homopolymer has a molecular weight ranging from about 5,000 to about 25,000. Even more preferred are the homopolymers in which $R^1$ is NF$_2$; and x is an integer having a value selected such that the homopolymer has a molecular weight raging from about 5,000 to 25,000. Also preferred are the homopolymers in which $R^1$ is H; and x is an integer having a value selected so that the homopolymer has a molecular weight ranging from about 5,000 to 25,000.

Of the copolymers within the scope of Formula II, certain structures are preferred, namely those in which $R^1$ is a combination of two or more functional groups selected from the following: H, CH$_3$, C$_2$H$_5$ and NF$_2$; and x is an integer having a value selected so that the copolymer has a molecular weight ranging from about

TABLE I

Properties of Mono- and Bis-NF$_2$-Oxetane

| STRUCTURE | BIS-NF$_2$-OXETANE | MONO-NF$_2$-OXETANE |
|---|---|---|
| FORM | SOLID-MP 44° C. | LIQUID-BP 37° C./5-mm |
| DENSITY | 1.55$^a$ | |
| | 1.68 g/cc (X-Ray) | |
| ΔH$_f$ | −43$^a$ (Kcal/100 g) | −57.1$^a$ (Kcal/100 g) |
| DECOMPOSITION ONSET | 208° C. (DSC) | |
| DECOMPOSITION MAX | 230° C. (DSC) | 205° C. (DTA) |
| HEAT FLOW | 4097 J/g | |
| SHOCK SENSITIVITY | >100 cm | >100 cm |
| SPARK | >1 Joule | >1 Joule |

$^a$Calculated Value 2,000 to 50,000. Further preferred are copolymers in which from about 10% to about 90% of $R^1$ is $NF_2$ and the remainder of $R^1$ is a substituent selected from the following functional groups: H, lower alkyl, $NO_2$, $ONO_2$, $N(R^2)NO_2$, where $R^2$ is H or a lower alkyl, and $N_3$; and x is an integer having a value selected so that the copolymer has a molecular weight ranging from about 5,000 to 25,000. More preferred are copolymers in which from about 30% to about 70% of $R^1$ is $NF_2$ and the remainder of $R^1$ is selected from the following functional groups: H, $NO_2$, $ONO_2$, $N(R^2)NO_2$, where $R_2$ is H or a lower alkyl, and $N_3$; and x is an integer having a value selected so that the copolymer has a molecular weight ranging from about 5,000 to 25,000. Also preferred are copolymers in which from about 30% to about 70% of $R^1$ is $NF_2$ and the remainder of $R^1$ is H; and x is an integer having a value selected so that the polymer has a molecular ranging from about 5,000 to 25,000.

Since propellants and explosives are preferably elastomeric in character, structures, both polymeric and non-polymeric, which are amorphous in character are preferred over those that are crystalline. One method of achieving this in the present invention is by the placement of asymmetric substituents on the neopentyl carbon. For example, with the $NF_2$-substituted oxetanes, when $R^1$ is a substituent other than an $NF_2$ group, non-crystalline, amorphous compounds are produced.

Copolymers are generally advantageous relative to homopolymers because the second mer unit, even in small amounts, substantially reduces stereoregularity. Homopolymers having a high degree of stereoregularity exhibit substantial chain folding, resulting in a compact structure which tends to be crystalline or highly viscous. However, when the monomer unit represented by Formula II is unsymmetrically substituted (i.e., $R^1$ is other than an $NF_2$ group), the homopolymer backbone will contain random asymmetry which will prevent crystallization.

Generally, it has been discovered that compounds containing neopentyl difluoroamino groups are readily prepared in high yield by the direct fluorination of blocked neopentyl amines. More specifically, the invention resides in a process for the preparation of compounds represented by Formula I, in which $R^1$ is a functional group including, but not limited to, H, lower alkyl, $NF_2$, $ONO_2$, $NO_2$, $N_3$ and $N(R^2)NO_2$, where $R^2$ is H or a lower alkyl. The process involves: (a) contacting a solution of a compound having the general formula:

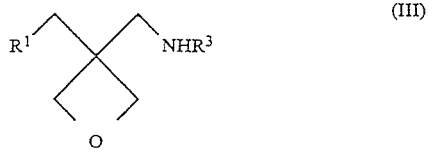

(III)

in which $R^3$ is a functional group including, but not limited to, CHO, $CONH_2$, $SO_3H$, and $CO_2R^4$ where $R^4$ is a lower alkyl, with fluorine gas to form a product mixture; and (b) recovering the compound represented by Formula I from said product mixture.

Within the scope of the above process, certain embodiments are preferred, namely those in which $R^3$ of the starting material represented by Formula III is a functional group selected from the following substituents: CHO, $CONH_2$, $SO_3H$, and $CO_2C_2H_5$. More preferred is the embodiment in which $R^3$ of the starting material is $CO_2C_2H_5$.

The temperature at which the reaction is conducted is not critical and can vary widely. In most applications, however, best results will be obtained when the reaction is conducted at a temperature of approximately 0° C. or below. In the most preferred methods, step (a) is performed at a temperature of approximately −5° C. or below.

In further preferred embodiments, the solution of step (a) is an organic solution, and the process further comprises contacting the product mixture with an aqueous solution of an alkali or alkaline metal ion prior to step (b). In still further preferred embodiments, the alkali or alkaline metal is a sodium ion, and the aqueous solution is a solution of sodium bicarbonate. Compounds prepared using the above process are recovered using standard methods and procedures known in the art.

Compounds corresponding to Formula I, for example, can be prepared by reacting 3-aminomethyl-3-methyloxetane with ethyl chloroformate to give the corresponding carbamate derivative, i.e., the ethyl carbamate of 3-aminomethyl-3-methyloxetane. Reaction of the carbamate in an inert solvent with fluorine will give the corresponding 3-difluoroaminomethyl-3-methyloxetane (i.e., mono-NF2-oxetane). The di(ethyl carbamate) of 3,3-bis(aminomethyl)oxetane is similarly reacted to give 3,3-bis(difluoroaminomethyl)oxetane (i.e., bis-NF2-oxetane).

The above examples are illustrative, and it will be readily apparent to the skilled artisan that other amine derivatives, such as amides, ureas, sulfamates, etc., can be used as starting materials to generate similar compounds.

The above reaction is generally career out in an inert solvent. Examples of inert solvents include, but are not limited to, water, acetonitrile and Freon-113. Additionally, the fluorine may be diluted with an inert gas to prevent excessively exothermic reactions. Concentrations between 1% and 50% fluorine will generally provide the best results. Diluents include, but are not limited to, nitrogen, helium and argon. In a presently preferred embodiment of this invention, a mixture of 10% fluorine in nitrogen is used.

The polymers of the present invention may be prepared in accordance with conventional procedures. Polyethers are formed from the oxetane monomers by cationic polymerization. This technique employs an initiator formed from an adduct of a substance such as a diol (e.g., 1,4-butanediol) and a catalyst for cationic polymerization. Such catalysts include, but are not limited to, boron trifluoride etherate, boron trifluoride, fluoroboric acid, or aluminum, phosphorus and antimony halides. The initiator reacts with one of the available monomers to form an initiating species, and polymerization proceeds by chain elongation until substantial. e.g., greater than 95%, exhaustion of the monomers.

The length of the chains is largely dependent upon the molar equivalents of monomers (m) and the initiators (n), the average chain length being approximately m/n mer units long. Generally, for use in binders, polyether chains are prepared having molecular weights (weight average) of between about 2,000 and about 25,000. Distribution of mer units throughout the polymer chains and polydispersity of the chains depends upon specific polymerization conditions. Polyethers in accordance with the present invention generally have polydispersities between about 1.5 and about 2.5. The molar ratio of mer units in the formed polyether generally reflects the molar ratio of available monomers, but may also depend upon the relative reactivities of the monomers in the polymerization reaction.

The polymers of the present invention are hydroxy-terminated, and thus they are curable with isocyanates through chain extension and cross-linkable to form elastomers. Polymeric chains which terminate at both ends with primary alcohol groups have a particular advantage since such groups are more reactive toward isocyanate groups during curing than the corresponding secondary and tertiary hydroxyl end groups. Elastomers are formed from the polyethers of the present invention by curing with isocyanates having a functionality of at least two, e.g., toluene diisocyanate. To promote chain elongation, at least one equivalent of an isocyanate is required. Preferably, cross-linking is also promoted by using an isocyanate of higher functionality or by adding a separate cross-linking agent, such as trimethylolethane or trimethylolpropane.

Table II lists the properties of the homopolymers formed from the mono-$NF_2$ and bis-$NF_2$ oxetanes, and the copolymer formed from a 50:50 molar mixture of the mono-$NF_2$ and bis-$NF_2$-oxetanes. The reaction of mono-$NF_2$-oxetane with boron trifluoride etherate and butane-1,4-diol gives essentially quantitative conversion to an amorphous polymer of 18,000 to 20,000 molecular weight. Anhydrous solutions of mono-$NF_2$-oxetane spontaneously polymerized at room temperature in methylene chloride, possibly due to the presence of some trace amounts of HF. The neat monomer, however, did not polymerize after several weeks at $-15°$ C. Solution polymerization of the bis-$NF_2$-substituted oxetane is slow at ambient temperature, but this monomer does form a homopolymer in bulk at higher temperatures. The homopolymer of bis-$NF_2$-oxetane is crystalline in form.

The mono-$NF_2$ and bis-$NF_2$-oxetane monomers readily form a copolymer using boron trifluoride etherate and butane-1,4-diol. The copolymer resulting from a 50:50 molar mixture of the mono-$NF_2$ and bis-$NF_2$-oxetane monomers is an amorphous oil. NMR analysis showed that the copolymer contains a random mixture of both monomers and that it is not a mixture of homopolymers. Additionally, the $NF_2$-substituted oxetanes of the present invention have similar reactivities to other oxetane compounds substituted at the 3-position with electron deficient pendant groups, such as, for example, azidomethyl and nitratomethyl-substituted oxetanes. These $NF_2$-substituted oxetane compounds are therefore able to form copolymers with a large variety of high-energy oxetane monomers. The polymers formed from these oxetane compounds may be tailored to meet specific molecular weight and energetic pendant group requirements. The polymers of the present invention may be subsequently cured to form energetic binders suitable for use in high-energy formulations.

TABLE II

Properties of Polymers Containing the Neopentyl Difluoroamino Group

| Polymer | Mono-$NF_2$ Homo-polymer | Bis-$NF_2$ Homopolymer | Copolymer of Mono-$NF_2$ and Bis-$NF_2$ (50:50) |
| --- | --- | --- | --- |
| Polymer Form | Amorphous Oil | Solid-MP 158° C. | Amorphous Oil |
| Gel Permeation Chromatography (Mw) | 18,300 | 4,125 | 21,400 |
| Polydispersity | 1.48 | 1.32 | 1.76 |
| Decomposition Onset (DSC) | 191.3° C. | 210.0° C. | 191.7° C. |
| Decomposition Maximum (DSC) | 230.7° C. | 222.3° C. | 219.8° C. |
| Heat Flow | 1851 J/g | 3031 J/g | 2490 J/g |

The invention will be described in greater detail by way of specific examples. The following examples are offered for illustrative purposes, and are intended neither to limit or define the invention in any manner.

EXAMPLE I

This example illustrates the preparation and properties of 3-difluoroaminomethyl-3-methyloxetane.

A. Preparation of Ethyl Carbamate of 3-Aminomethyl-3-methyloxetane

A solution of 3-aminomethyl-3-methyloxetane (10.1 g, 0.10 mol) in 50 mL of water containing sodium hydroxide (8.07 g, 0.2 mol) was cooled to 0° C., and ethyl chloroformate (22.38 g, 0.2 mol) was added dropwise over 1 h at a rate such that the temperature of the mixture did not exceed 2° C. The mixture was stirred for an additional 1 h at 0° C., and then extracted with three portions of 100 mL of methylene chloride. The combined organic extracts were then dried over magnesium sulfate and the solvent was removed by evaporation to yield 17.6 g of the ethyl carbamate of 3-aminomethyl-3-methyloxetane, representing a 99% yield.

An analytical sample was prepared by distillation at 106–108° C. and 0.25 mm pressure. IR (DRIFTS): 3325, 2965, 1703, 1543, 1249 cm$^{-1}$. NMR: $^1$H NMR 1.25 (t, J 7 Hz, 3 H), 1.30 (s, 3 H), 3.36 (d, J=6 Hz, 2 H), 4.14 (q, J=7 Hz, 2 H), 4.36 (d, J=6 Hz, 2 H), 4.47 (d, J=6 Hz, 2 H); $^{13}$C NMR 14.623, 21.824, 40.105, 47.480, 61.031, 80.136. Elemental analysis calculated for $C_8H_{15}NO_3$: C, 55.47, H, 8.73; N, 8.09. Found: C, 54.57; H, 8.45; N, 8.25.

B. Preparation of 3-Difluoroaminomethyl-3-methyloxetane

A mixture of 10% fluorine in nitrogen was passed at 150–250 mL/min through a solution of the ethyl carbamate of 3-aminomethyl-3-methyloxetane (17.32 g, 0.1 mole) in 170 mL of acetonitrile at $-10°$ C. After 4.5 h when $^{19}$F NMR analysis showed that the monofluorinated material was consumed ($-40$ ppm), the fluorine flow was discontinued. The reaction mixture was purged with nitrogen for 10 minutes and added to ice water (1 L). The bottom organic layer was separated, diluted with 35 mL of methylene chloride, washed with water and 5% aqueous sodium bicarbonate solution, and dried over magnesium sulfate. The solvent was removed by evaporation to yield 13.1 g (96% yield) of crude 3-difluoroaminomethyl-3-methyloxetane.

An analytical sample was purified by distillation at 37° C. and 5 mm pressure. Differential thermal analysis (DTA) showed maximum decomposition at 215° C.; Bureau of Mines Impact Sensitivity > 100 cm; NMR: $^1$H NMR 1.56 (s, 3 H), 3.74 (t, J=27.8 Hz, 2 H), 4.36 (d, J=6.0 Hz, 2 H), 4.56 (d, J=6.0 Hz, 2 H); $^{13}$C NMR 21.528, 37.303 (t, J=12.5 Hz), 71.377(t, J=5.6 Hz), 80.234; $^{19}$F NMR 57.49 (t, J=27.8 Hz); Elemental analysis calculated for $C_5H_9NOF_2$: C, 43.79, H, 6.62; Found: C, 44.05; H, 6.75.

EXAMPLE II

This example illustrates the preparation and properties of 3,3-bis(difluoroaminomethyl)oxetane.

A. Preparation of Di(ethylcarbamate) of 3,3-bis(aminomethyl)oxetane

A solution of 3,3-bis(aminomethyl)oxetane (69.7 g, 0.60 mol) in 350 mL of water containing sodium hydroxide (72.65 g, 1.8 mol) was cooled to 0° C., and ethyl chloroformate (201.4 g, 1.8 mol) was added dropwise over 2 h at a rate such that the temperature of the mixture did not exceed 2° C. The mixture was stirred for an additional 2 h at 0° C., and the product was extracted with 300 mL of methylene chloride. The organic layer was separated, dried over magnesium sulfate and evaporated to give 153.2 g of the di(ethyl carbamate) of 3,3-bis(aminomethyl)oxetane, representing a 98% yield.

An analytical sample was prepared by recrystallization from carbon tetrachloride, mp 96–96.5° C. IR (Drifts): 3338, 2900, 1694, 1536, 1255, 1030 cm$^{-1}$; NMR: $^1$H NMR 1.23 (t, J=7 Hz, 6 H), 3.49 (d, J=6 Hz, 4, H), 4.10 (q, J=7 Hz, 4 H), 4.40 (s, 4 H); $^{13}$C NMR 14.591, 43.644, 44.447, 61.135, 77.303, 157.686; Elemental analysis calculated for $C_{11}H_{20}N_2O_5$: C, 50.76; H, 7.75; N, 10.76; Found: C, 50.51, H, 7.65; N, 10.69.

B. Preparation of 3,3-Bis(difluoroaminomethyl)oxetane

A mixture of 10% fluorine in nitrogen was passed at 100–200 mL/min through a solution of the all(ethyl carbamate) of 3,3-bis(aminomethyl)oxetane (6.51 g, 0.025 mole) in 100 mL of acetonitrile at −20° C. After 4.5 h when $^{19}$F NMR analysis showed that the monofluorinated material was consumed (−40 ppm), the fluorine flow was discontinued. The reaction mixture was purged with nitrogen for 10 minutes and added to ice water (1 L). The bottom organic layer was separated and diluted with 35 mL of methylene chloride, washed with water and 5% aqueous sodium bicarbonate solution, and dried over magnesium sulfate. The solvent was removed by evaporation to give 3.92 g (83% yield) of crude 3,3-bis(difluoroaminomethyl)oxetane, mp 43.5–44.5° C. ($CH_2Cl_2$).

An analytical sample was purified by sublimation at 50–60° C. and 0.05 mm pressure. Differential scanning calorimetry (20° C./min, nitrogen) showed an onset of decomposition at 208° C., and a maximum at 230.8° C.; Bureau of Mines Impact Sensitivity>100 cm; NMR: $^1$H NMR 4.00 (t, J=28.0 Hz, 4 H), 4.60 (s, 4 H); $^{13}$C NMR 39.490, 67.398 (t, J=7.5 Hz), 77.230 (t, J=14.9 Hz); $^{19}$F NMR 56.37 (t, J=27.8 Hz); Elemental analysis calculated for $C_5H_8N_2OF_4$: C, 31.92; H, 4.29; N, 14.89; Found: C, 31.58; H, 4.17; N, 14.73.

EXAMPLE III

This example illustrates the preparation and properties of the homopolymer poly(3-difluoroaminomethyl-3-methyloxetane).

A. Preparation of Poly(3-difluoroaminomethyl-3-methyloxetane)

A mixture of butane-1,4-diol (47 mg, 0.52 mmol) and boron trifluoride etherate (0.148 g, 1.04 mmol) in 40 mL of methylene chloride was stirred under nitrogen at ambient temperature for 30 minutes and then cooled to 0° C. A solution of 3-difluoroaminomethyl-3-methyloxetane (5.0 g, 0.0365 mol) in methylene chloride (10 mL) was added over 10 min and the mixture was allowed to stir for 22 h. The solution was quenched with 50 mL of water. The organic layer was separated and dried over magnesium sulfate. The solvent was removed by evaporation, leaving 5.0 g of poly(3-difluoroaminomethyl-3-methyloxetane), as an oil, representing a 100% yield. The oil was dissolved in 6 mL of methylene chloride and added dropwise to 75 mL of methanol at ambient temperature. The solvents were decanted and the residual oil was dried in vacuo for 24 h.

Differential scanning calorimetry showed a glass transition temperature ($T_g$) at −21° C., an onset of decomposition at 191.3° C., and a maximum at 230.79° C.; Heat Flow: 1851 Joules/g; Thermogravimetric analysis (TGA) showed 0.32% weight loss after 15 hours at 100° C.; NMR: $^1$H NMR 1.04 (s), 3.24 (d, J=9.0 Hz) 3.30 (d, J=9 Hz), 3.51 (t, J=30.5 Hz); $^{13}$C NMR 18.108, 18.211, 18.577, 26.3537, 39.714 (t, J=6.4 Hz), 68.085, 69.051 (t, J=5.1 Hz), 70.1641, 71.217, 72.969, 74,221, 75,790; $^{19}$F NMR 63.7 (t, J=30.6 Hz); Gel permeation chromatography (GPC): Number average molecular weight (Mn) 12000, Weight average molecular weight (Mw) 18300; Polydispersity (Disp.): 1.48.

EXAMPLE IV

This example illustrates the preparations and properties of the homopolymer of poly(3,3-bis(difluoroaminomethyl)oxetane).

A. Preparation of Poly(3,3-bis(difluoroaminomethyl)oxetane)

A mixture of butane-1,4-diol (33 mg, 0.37 mmol) and boron trifluoride etherate (0.107 g, 0.75 mmol) in 40 mL of methylene chloride was stirred under nitrogen at ambient temperature for 1 h and then cooled to 0° C. A solution of 3,3-bis(difluoroaminomethyl) oxetane (3.50 g, 0.0186 mol) in 10 mL of methylene chloride was added over 2 min, and the mixture was allowed to stir for 48 h. NMR analysis of the reaction mixture show no reaction had occurred. Boron trifluoride etherate (0.10 g, 0.74 mmol) was added and the mixture was stirred for an additional 48 h during which time no polymer formation was noted by NMR analysis. The solvent was evaporated at 40° C. during which time polymerization occurred to give a white methylene chloride insoluble solid. The solid was washed with 50 mL of water, and dried to give 3.5 g (100%)of poly(3,3-bis(difluoroaminomethyl)oxetane), mp 158–162° C.

Differential scanning calorimetry showed a $T_g$ at 130.78° C., an onset of decomposition at 210° C. and a maximum at 222.3° C.; Heat Flow: 3013 Joules/g; NMR: $^1$H NMR 3.61 (s); 3.92 (t, J=30.2 Hz); $^{13}$C NMR 43.104 (t, J=7.5 Hz), 62.011, 67.026 (Br 10.2 Hz at ½ Height), 71.040; $^{19}$F NMR 64.0 (t, J=29.6 Hz); GPC: Mn 3199, Mw 4125; Disp.: 1.32.

EXAMPLE V

This example illustrates the preparation and properties of the copolymerization of 3-difluoroaminomethyl-3-methyloxetane and 3,3-bis(difluoroaminomethyl)oxetane.

A. Preparation of the Copolymer of 3-difluoroaminomethyl-3-methyloxetane and 3,3-bis-(difluoroaminomethyl)-oxetane A mixture of butane-1,4-diol (15 mg, 0.17 mmol) and boron trifluoride etherate (50 mg, 0.35 mmol) in 40 mL of methylene chloride was stirred under nitrogen at ambient temperature for 30 minutes. A solution of 3-difluoroaminomethyl-3-methyloxetane (0.36 g, 2.63 mmol) and 3,3-bis(difluoroaminomethyl)oxetane (0.49 g, 2.63 mmol) in 10 mL of methylene chloride was added in bulk. An exothermic reaction occurred and the mixture was allowed to stir for 22 h. The solution was quenched with 5 mL of water. The organic layer was separated and dried over magnesium sulfate. The solvent was removed by evaporation to give 0.85 g, representing a 100% yield, of difluoroaminomethyloxetane copolymer as an oil.

The oil was dissolved in 6 mL of methylene chloride and added dropwise to 75 mL of methanol at ambient temperature. The solvents were decanted and the residual oil was dried in vacuo for 24 h.

Differential scanning calorimetry showed an onset of decomposition at 191.76° C. and a maximum at 219.84° C.; Heat Flow: 2490 Joules/g; NMR: $^1$H NMR 1.04 (s), 3.28–3.60 (m), 3.51 (t, J=29 Hz), 3.69 (t, J=29 Hz); $^{13}$C NMR 18.526, 39.667 (m), 41.050, 66.173 (m), 69.038, 70.325 (m), 71.501, 73.998, 74.166; $^{19}$F NMR 63.89 (m, 4 F) 63.19 (m, 2 F). GPC: Mn 12000, Mw 21400; Disp.: 1.76.

The foregoing is offered primarily for purposes of illustration. It will be readily apparent to those skilled in the art that the operating conditions, materials, procedural steps and other parameters of the systems described herein may be further modified or substituted in various ways without departing from the spirit and scope of the invention.

What is claimed is:

1. A compound having the formula

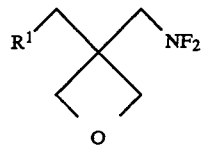

in which $R^1$ is a member selected from the group consisting of H and $NF_2$.

2. A compound in accordance with claim 1 in which $R^1$ is H.

3. A compound in accordance with claim 1 in which $R^1$ is $NF_2$.

* * * * *